(12) United States Patent
Hyakutake

(10) Patent No.: US 10,017,437 B2
(45) Date of Patent: Jul. 10, 2018

(54) METHOD FOR PURIFYING FLUORINATED HYDROCARBON COMPOUND

(71) Applicant: ZEON CORPORATION, Chiyoda-ku, Tokyo (JP)

(72) Inventor: Munehiro Hyakutake, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 15/541,480

(22) PCT Filed: Jan. 15, 2016

(86) PCT No.: PCT/JP2016/051111
§ 371 (c)(1),
(2) Date: Jul. 4, 2017

(87) PCT Pub. No.: WO2016/117463
PCT Pub. Date: Jul. 28, 2016

(65) Prior Publication Data
US 2017/0369404 A1    Dec. 28, 2017

(30) Foreign Application Priority Data
Jan. 22, 2015 (JP) ................................. 2015-010538

(51) Int. Cl.
*C07C 17/389* (2006.01)

(52) U.S. Cl.
CPC .................................. *C07C 17/389* (2013.01)

(58) Field of Classification Search
CPC ..................................................... C07C 17/389
See application file for complete search history.

(56) References Cited

FOREIGN PATENT DOCUMENTS

JP       2014024785 A       2/2014
WO     WO -2015093527 A1 *  6/2015 ............ C07C 17/389

OTHER PUBLICATIONS

WO2015093527A1, Jun. 25, 2015, pp. 1-6; English translation (Year: 2015).*
Itochu "Ion Exchange Resins" Jul. 15, 2013, pp. 1-13 (Year: 2013).*
George A. Olah et al., "Synthetic Methods and Reactions. 63. Pyridinium Poly(hydrogen fluoride) (30% Pyridine—70% Hydrogen Fluoride): A Convenient Reagent for Organic Fluorination Reactions", J. Org. Chem., 1979, vol. 44, No. 22, pp. 3872-3881.

* cited by examiner

*Primary Examiner* — Medhanit W Bahta
(74) *Attorney, Agent, or Firm* — Kenja IP Law PC

(57) ABSTRACT

The present invention is a method for purifying a fluorohydrocarbon compound comprising bringing a crude saturated fluorohydrocarbon compound having 4 or 5 carbon atoms into contact with a salt-type strongly acidic ion-exchange resin to remove water from the crude saturated fluorohydrocarbon compound. The present invention provides a method for purifying a fluorohydrocarbon compound that can sufficiently remove water from the fluorohydrocarbon compound without causing a decrease in the purity of the fluorohydrocarbon compound due to decomposition.

4 Claims, No Drawings

METHOD FOR PURIFYING FLUORINATED HYDROCARBON COMPOUND

TECHNICAL FIELD

The present invention relates to a method for purifying a fluorohydrocarbon compound.

BACKGROUND ART

A fluorohydrocarbon compound exhibits excellent etching selectivity with respect to the etching target material, and has been used in recent years as a dry etching gas for producing a semiconductor device.

A fluorohydrocarbon compound that is used in the semiconductor production field and the like is required to have a reduced water content in order to achieve high etching selectivity.

A fluorohydrocarbon compound may be dehydrated using a molecular sieve (hereinafter may be referred to as "MS") that is a common dehydrating agent.

However, isomerization and a decomposition reaction easily occur when a fluorohydrocarbon compound is brought into contact with an MS, whereby the purity of the fluorohydrocarbon compound decreases.

In order to solve this problem, Patent Literature 1 discloses a method for purifying a fluorohydrocarbon compound that includes bringing a specific crude fluorohydrocarbon compound into contact with a hydrous metal salt of a synthetic crystalline aluminosilicate having an average pore size of 3 Å to remove water from the crude fluorohydrocarbon compound, for example.

CITATION LIST

Patent Literature

Patent Literature 1: JP-A-2014-24785

SUMMARY OF INVENTION

Technical Problem

Patent Literature 1 states that the purification method disclosed in Patent Literature 1 makes it possible to sufficiently remove water from the crude fluorohydrocarbon compound, and suppress the production of a dehydrofluorinated product due to decomposition of the fluorohydrocarbon compound to obtain a fluorohydrocarbon compound having high purity.

However, a fluorohydrocarbon compound having higher purity has been desired along with a recent improvement in etching technology.

The invention was conceived in view of the above situation. An object of the invention is to provide a method for purifying a fluorohydrocarbon compound that can sufficiently remove water from the fluorohydrocarbon compound without causing a decrease in the purity of the fluorohydrocarbon compound due to decomposition.

Solution to Problem

The inventor conducted extensive studies with regard to a method for purifying a fluorohydrocarbon compound in order to solve the above problem. As a result, the inventor found that it is possible to sufficiently remove water from a fluorohydrocarbon compound without causing a decrease in the purity of the fluorohydrocarbon compound due to decomposition, by bringing a crude saturated fluorohydrocarbon compound having 4 or 5 carbon atoms into contact with a specific ion-exchange resin. This finding has led to the completion of the invention.

One aspect of the invention provides the following method for purifying a fluorohydrocarbon compound (see (1) to (3)).

(1) A method for purifying a fluorohydrocarbon compound including bringing a crude saturated fluorohydrocarbon compound having 4 or 5 carbon atoms into contact with a salt-type strongly acidic ion-exchange resin to remove water from the crude saturated fluorohydrocarbon compound.

(2) The method according to (1), wherein the saturated fluorohydrocarbon compound having 4 or 5 carbon atoms is a compound represented by the following formula (1) or (2), $$C_4H_aF_b \qquad (1)$$

$$C_5H_cF_d \qquad (2)$$

wherein a and b represent a positive integer, provided that a+b is equal to or less than 10, and c and d represent a positive integer, provided that c+d is equal to or less than 12.

(3) The method according to (1) or (2), wherein the salt-type strongly acidic ion-exchange resin is a resin that includes a cation selected from the group consisting of a sodium ion and a calcium ion, and a sulfo group.

Advantageous Effects of Invention

One aspect of the invention thus provides a method for purifying a fluorohydrocarbon compound that can sufficiently remove water from the fluorohydrocarbon compound without causing a decrease in the purity of the fluorohydrocarbon compound due to decomposition.

DESCRIPTION OF EMBODIMENTS

A method for purifying a fluorohydrocarbon compound (hereinafter may be referred to as "purification method") according to one embodiment of the invention includes bringing a crude saturated fluorohydrocarbon compound having 4 or 5 carbon atoms into contact with a salt-type strongly acidic ion-exchange resin to remove water from the crude saturated fluorohydrocarbon compound.

Crude Fluorohydrocarbon Compound Having 4 or 5 Carbon Atoms

The treatment target of the purification method according to one embodiment of the invention is a crude saturated fluorohydrocarbon compound having 4 or 5 carbon atoms (hereinafter may be referred to as "crude product").

Examples of the saturated fluorohydrocarbon compound having 4 or 5 carbon atoms included in the crude product include compounds respectively represented by the following formulas (1) and (2).

$$C_4H_aF_b \qquad (1)$$

$$C_5H_cF_d \qquad (2)$$

a and b in the formula (1) represent a positive integer, provided that a+b is equal to or less than 10. It is preferable that a≥b since such a compound is suitable as a dry etching gas.

Examples of the fluorohydrocarbon compound represented by the formula (1) include a linear fluorohydrocarbon compound having 4 carbon atoms, such as $C_4H_9F$, $C_4H_8F_2$, $C_4H_7F_3$, $C_4H_6F_4$, and $C_4H_5F_5$; a cyclic fluorohydrocarbon compound having 4 carbon atoms, such as $C_4H_7F$, $C_4H_6F_2$, and $C_4H_5F_3$; and the like.

c and d in the formula (2) represent a positive integer, provided that c+d is equal to or less than 12. It is preferable that c≥d since such a compound is suitable as a dry etching gas.

Examples of the fluorohydrocarbon compound represented by the formula (2) include a linear fluorohydrocarbon compound having 5 carbon atoms, such as $C_5H_{11}F$, $C_5H_{10}F_2$, $C_5H_9F_3$, $C_5H_8F_4$, $C_5H_7F_5$, and $C_5H_6F_6$; a cyclic fluorohydrocarbon compound having 5 carbon atoms, such as $C_5H_9F$, $C_5H_8F_2$, $C_5H_7F_3$, and $C_5H_6F_4$; and the like.

A linear saturated fluorohydrocarbon compound having 4 or 5 carbon atoms is preferable as the fluorohydrocarbon compound having 4 or 5 carbon atoms.

Examples of the linear saturated fluorohydrocarbon compound having 4 or 5 carbon atoms include a compound represented by $C_4H_9F$, such as 1-fluorobutane, 2-fluorobutane, 1-fluoro-2-methylpropane, and 2-fluoro-2-methylpropane; a compound represented by $C_4H_8F_2$, such as 1,4-difluorobutane, 2,2-difluorobutane, and 2,3-difluorobutane; a compound represented by $C_4H_7F_3$, such as 1,1,2-trifluorobutane; a compound represented by $C_4H_6F_4$, such as 1,1,1,2-tetrafluorobutane; a compound represented by $C_4H_5F_5$, such as 1,1,1,3,3-pentafluorobutane; a compound represented by $C_5H_{11}F$, such as 1-fluoropentane, 2-fluoropentane, 3-fluoropentane, 1-fluoro-2-methylbutane, 1-fluoro-3-methylbutane, 2-fluoro-2-methylbutane, 2-fluoro-3-methylbutane, and 1-fluoro-2,2-dimethylpropane; a compound represented by $C_5H_{10}F_2$, such as 1,5-difluoropentane, 2,4-difluoropentane, and 3,3-difluoropentane; a compound represented by $C_5H_9F_3$, such as 1,1,1-trifluoropentane; a compound represented by $C_5H_8F_4$, such as 1,1,1,2-tetrafluoropentane; and the like.

The purity of the fluorohydrocarbon compound included in the crude product used in connection with one embodiment of the invention is normally 99.0 to 99.9 vol %, and preferably 99.5 to 99.9 vol %.

The water content in the crude product is normally 100 to 5,000 ppm by volume, and preferably 100 to 3,000 ppm by volume.

When the purity of the fluorohydrocarbon compound included in the crude product, and the water content in the crude product are within the above ranges, it is possible to efficiently produce a high-purity fluorohydrocarbon compound that is suitable as a dry etching gas.

The purity of the fluorohydrocarbon compound refers to a value calculated from the peak area determined by gas chromatography that utilizes a flame ionization detector (FID). The water content refers to a value determined by FT-IR.

The crude product used in connection with one embodiment of the invention may be produced (obtained) using a known production method. For example, crude 2-fluorobutane may be produced (obtained) using the method described in J. Org. Chem, 44 (22), 3872 (1979). A commercially-available product may also be used as the crude fluorohydrocarbon compound.

Salt-type Strongly Acidic Ion-exchange Resin

In one embodiment of the invention, the salt-type strongly acidic ion-exchange resin is used as a dehydrating agent. The term "strongly acidic ion-exchange resin" used herein refers to an ion-exchange resin that includes a strongly acidic functional group. The term "strongly acidic functional group" used herein refers to a functional group that has a pKa at 25° C. of 1 or less when protonated. Examples of the strongly acidic functional group include a sulfo group (i.e., an atomic group represented by —$SO_3H$). Examples of the strongly acidic ion-exchange resin include a copolymer of styrenesulfonic acid and divinylbenzene, and the like.

According to one embodiment of the invention, it is possible to sufficiently remove water from the fluorohydrocarbon compound without causing a decrease in the purity of the fluorohydrocarbon compound due to decomposition, by utilizing the strongly acidic ion-exchange resin as a dehydrating agent.

A salt-type (i.e., neutralized) strongly acidic ion-exchange resin is used as the strongly acidic ion-exchange resin. It is possible to sufficiently remove water from the fluorohydrocarbon compound without causing a decrease in the purity of the fluorohydrocarbon compound due to decomposition, by utilizing the salt-type strongly acidic ion-exchange resin.

The cation that is included in the salt-type strongly acidic ion-exchange resin is not particularly limited. Examples of the cation that is included in the salt-type strongly acidic ion-exchange resin include a sodium ion, a potassium ion, a magnesium ion, a calcium ion, a barium ion, an ammonium ion, and the like. Among these, a sodium ion and a calcium ion are preferable.

It is preferable that the salt-type strongly acidic ion-exchange resin be a resin that includes a cation selected from the group consisting of a sodium ion and a calcium ion, and a sulfo group.

A gel-type strongly acidic ion-exchange resin, a porous strongly acidic ion-exchange resin, a highly porous strongly acidic ion-exchange resin, and the like are known as the strongly acidic ion-exchange resin. Any of these strongly acidic ion-exchange resins may be used in connection with one embodiment of the invention. It is preferable to use a gel-type strongly acidic ion-exchange resin since water can be more efficiently removed.

The effective diameter, the particle size range, the degree of crosslinking, and the like of the ion-exchange resin are not particularly limited, and may be appropriately determined taking account of the intended use.

It is preferable that the strongly acidic ion-exchange resin has been dried until the weight has reached a specific value. The drying conditions are not particularly limited. For example, the strongly acidic ion-exchange resin may be subjected to hot-air drying at 120° C. for 3 hours to obtain a strongly acidic ion-exchange resin that is suitable for the method according to one embodiment of the invention.

Purification Method

The purification method according to one embodiment of the invention includes bringing the crude product into contact with the salt-type strongly acidic ion-exchange resin to remove water from the crude product.

The crude product may be brought into contact with the salt-type strongly acidic ion-exchange resin using (1) an immersion method that puts the crude product in a container that holds the salt-type strongly acidic ion-exchange resin, and allows the mixture to stand, (2) a circulation method that circulates the crude product through a pipe charged with the salt-type strongly acidic ion-exchange resin to bring the crude product into contact with the salt-type strongly acidic ion-exchange resin, or the like. An appropriate method may be appropriately selected from the immersion method, the circulation method, and the like taking account of the intended use.

The salt-type strongly acidic ion-exchange resin is preferably used in an amount of 5 to 80 parts by weight, and more preferably 10 to 50 parts by weight, based on 100 parts by weight of the crude product. If the salt-type strongly acidic ion-exchange resin is used in too small an amount, there is a tendency that the dehydration performance decreases. If the salt-type strongly acidic ion-exchange resin is used in too large an amount, a decrease in productivity may occur although an improvement in effect is not achieved.

The temperature at which the crude product is brought into contact with the salt-type strongly acidic ion-exchange resin is determined taking account of the boiling point of the fluorohydrocarbon compound. If the crude product is brought into contact with the salt-type strongly acidic ion-exchange resin at a temperature higher than the boiling point of the fluorohydrocarbon compound, a decrease in yield may occur. Therefore, it is preferable to bring the crude product into contact with the salt-type strongly acidic ion-exchange resin at a temperature lower than the boiling point of the fluorohydrocarbon compound. The temperature at which the crude product is brought into contact with the salt-type strongly acidic ion-exchange resin is preferably 0 to 50° C., and more preferably 0 to 30° C., from the viewpoint of productivity.

The crude product is normally brought into contact with the salt-type strongly acidic ion-exchange resin for 1 to 72 hours.

A known method for purifying a fluorohydrocarbon compound (e.g., a dehydration method that uses an MS as a dehydrating agent) has a problem in that a dehydrofluorinated product is produced due to a decomposition reaction.

Examples of the dehydrofluorinated product of 2-fluorobutane include (E)-2-butene, (Z)-2-butene, and 1-butene.

Since the purification method according to one embodiment of the invention can suppress the decomposition of the fluorohydrocarbon compound, a dehydrofluorinated product is not produced, and a decrease in purity does not occur.

The purity of the purified fluorohydrocarbon compound obtained by the purification method according to one embodiment of the invention is normally 99.0 vol % or more, and preferably 99.9 vol % or more. The purity of the purified fluorohydrocarbon compound is equal to or higher than that of the crude product.

The water content in the purified fluorohydrocarbon compound is normally 50 ppm by volume or less, preferably 30 ppm by volume or less, and more preferably 20 ppm by volume or less.

As described above, the method according to one embodiment of the invention can sufficiently remove water from the fluorohydrocarbon compound without causing a decrease in the purity of the fluorohydrocarbon compound due to decomposition.

The purified fluorohydrocarbon compound obtained by the method according to one embodiment of the invention may suitably be used as a dry etching gas that is used to produce a semiconductor device.

EXAMPLES

The invention is further described below by way of examples. Note that the invention is not limited to the following examples.

The dehydrating agents listed below were used.
Ion-exchange resin (1): DIAION SK1B manufactured by Mitsubishi Chemical Corporation (gel type, sulfo group, sodium ion, degree of crosslinking: 8%)
Ion-exchange resin (2): DIAION SK1B-H manufactured by Mitsubishi Chemical Corporation (gel type, sulfo group, hydrogen ion, degree of crosslinking: 8%) (the counter ion of the functional group was changed to a calcium ion using a specific treatment)
Ion-exchange resin (3): DIAION SK104 manufactured by Mitsubishi Chemical Corporation (gel type, sulfo group, sodium ion, degree of crosslinking: 4%)
Ion-exchange resin (4): DIAION PK216 manufactured by Mitsubishi Chemical Corporation (porous type, sulfo group, sodium ion, degree of crosslinking: 8%)
Ion-exchange resin (5): DIAION SK1BH manufactured by Mitsubishi Chemical Corporation (gel type, sulfo group, hydrogen ion, degree of crosslinking: 8%)
Ion-exchange resin (6): DIAION WK40L manufactured by Mitsubishi Chemical Corporation (porous type, carboxy group, hydrogen ion) (the counter ion of the functional group was changed to a calcium ion using a specific treatment)
Molecular sieve (1): MS3A manufactured by Wako Pure Chemical Industries, Ltd. (cat. No. 133-08645)

The ion-exchange resins (1) to (6) were subjected to hot-air drying at 120° C. for 3 hours.

The molecular sieve (1) was subjected to hot-air drying at 450° C. for 3 hours.

Measurement of Water Content in Crude Product or Purified Product

The water content in the crude product or the purified product was determined by FT-IR using the following measurement device.
Measurement device: IG-1000 manufactured by Otsuka Electronics Co., Ltd. (cell length: 10 m)

The purified product (i.e., the sample in which the dehydrating agent had been immersed for 24 hours) was evaluated in accordance with the following standard.
Good: The water content in the purified product was less than 100 ppm.
Fair: The water content in the purified product was 100 ppm or more and less than 500 ppm.
Bad: The water content in the purified product was 500 ppm or more.

Measurement of Purity of Fluorohydrocarbon Compound

The purity of the fluorohydrocarbon compound included in the crude product or the purified product was determined by gas chromatography using the following measurement device.
Measurement device: Agilent (registered trademark) 7890-A manufactured by Agilent Technologies
Column: Inert Cap-1 manufactured by GL Sciences Inc. (length: 60 m, inner diameter: 250 μm, thickness: 1.5 μm)
Detector: FID The purification method was evaluated in accordance with the following standard based on the experimental results.
Good: The purity of the fluorohydrocarbon compound included in the purified product was equal to or higher than that of the crude product.
Bad: The purity of the fluorohydrocarbon compound included in the purified product was lower than that of the crude product.

Example 1

A glass screw cap bottle was charged with 10.0 g of the crude product for which the water content and the purity of 2-fluorobutane had been measured, and 1.0 g of the ion-exchange resin (1) was immersed therein. After allowing the mixture to stand at 23° C. for 24 hours, the water content in the purified product, and the purity of 2-fluorobutane were measured. The measurement results are listed in Table 1.

Example 2

An immersion treatment was performed in the same manner as in Example 1, except that the ion-exchange resin (2) was used instead of the ion-exchange resin (1), and the water content in the purified product, and the purity of 2-fluorobutane were measured. The measurement results are listed in Table 1.

Example 3

An immersion treatment was performed in the same manner as in Example 1, except that the ion-exchange resin (3) was used instead of the ion-exchange resin (1), and the water content in the purified product, and the purity of 2-fluorobutane were measured. The measurement results are listed in Table 1.

Example 4

An immersion treatment was performed in the same manner as in Example 1, except that the ion-exchange resin (4) was used instead of the ion-exchange resin (1), and the water content in the purified product, and the purity of 2-fluorobutane were measured. The measurement results are listed in Table 1.

Example 5

An immersion treatment was performed in the same manner as in Example 1, except that 2,2-difluorobutane was used instead of 2-fluorobutane, and the water content in the purified product, and the purity of 2,2-difluorobutane were measured. The measurement results are listed in Table 1.

Example 6

An immersion treatment was performed in the same manner as in Example 4, except that 2,2-difluorobutane was used instead of 2-fluorobutane, and the water content in the purified product, and the purity of 2,2-difluorobutane were measured. The measurement results are listed in Table 1.

Example 7

An immersion treatment was performed in the same manner as in Example 1, except that 2-fluoropentane was used instead of 2-fluorobutane, and the water content in the purified product, and the purity of 2-fluoropentane were measured. The measurement results are listed in Table 1.

Example 8

An immersion treatment was performed in the same manner as in Example 4, except that 2-fluoropentane was used instead of 2-fluorobutane, and the water content in the purified product, and the purity of 2-fluoropentane were measured. The measurement results are listed in Table 1.

Example 9

An immersion treatment was performed in the same manner as in Example 1, except that 1,1,1,3,3-pentafluorobutane was used instead of 2-fluorobutane, and the water content in the purified product, and the purity of 1,1,1,3,3-pentafluorobutane were measured. The measurement results are listed in Table 1.

Example 10

An immersion treatment was performed in the same manner as in Example 4, except that 1,1,1,3,3-pentafluorobutane was used instead of 2-fluorobutane, and the water content in the purified product, and the purity of 1,1,1,3,3-pentafluorobutane were measured. The measurement results are listed in Table 1.

Comparative Example 1

An immersion treatment was performed in the same manner as in Example 1, except that the ion-exchange resin (5) was used instead of the ion-exchange resin (1), and the water content in the purified product, and the purity of 2-fluorobutane were measured. The measurement results are listed in Table 1.

Comparative Example 2

An immersion treatment was performed in the same manner as in Example 1, except that the ion-exchange resin (6) was used instead of the ion-exchange resin (1), and the water content in the purified product, and the purity of 2-fluorobutane were measured. The measurement results are listed in Table 1.

Comparative Example 3

An immersion treatment was performed in the same manner as in Example 1, except that the molecular sieve (1) was used instead of the ion-exchange resin (1), and the water content in the purified product, and the purity of 2-fluorobutane were measured. The measurement results are listed in Table 1.

Comparative Example 4

An immersion treatment was performed in the same manner as in Comparative Example 3, except that 2,2-difluorobutane was used instead of 2-fluorobutane, and the water content in the purified product, and the purity of 2,2-difluorobutane were measured. The measurement results are listed in Table 1.

Comparative Example 5

An immersion treatment was performed in the same manner as in Comparative Example 3, except that 2-fluoropentane was used instead of 2-fluorobutane, and the water content in the purified product, and the purity of 2-fluoropentane were measured. The measurement results are listed in Table 1.

Comparative Example 6

An immersion treatment was performed in the same manner as in Comparative Example 3, except that 1,1,1,3,3-pentafluorobutane was used instead of 2-fluorobutane, and the water content in the purified product, and the purity of 1,1,1,3,3-pentafluorobutane were measured. The measurement results are listed in Table 1.

TABLE 1

| | Fluorohydrocarbon compound | Dehydrating agent | | | Water content (ppm) | | | Purity (%) | | |
|---|---|---|---|---|---|---|---|---|---|---|
| | | Type | Functional group | Cation | Before treatment | After treatment | Evaluation | Before treatment | After treatment | Evaluation |
| Example 1 | 2-Fluorobutane | Ion-exchange resin (1) | Sulfo group | Sodium ion | 1,007 | 40 | Good | 99.93 | 99.93 | Good |
| Example 2 | | Ion-exchange resin (2) | Sulfo group | Calcium ion | 1,007 | 35 | Good | 99.93 | 99.93 | Good |
| Example 3 | | Ion-exchange resin (3) | Sulfo group | Sodium ion | 1,007 | 80 | Good | 99.93 | 99.93 | Good |
| Example 4 | | Ion-exchange resin (4) | Sulfo group | Sodium ion | 1,007 | 400 | Fair | 99.93 | 99.93 | Good |
| Example 5 | 2,2-Difluorobutane | Ion-exchange resin (1) | Sulfo group | Sodium ion | 990 | 45 | Good | 99.91 | 99.91 | Good |
| Example 6 | | Ion-exchange resin (4) | Sulfo group | Sodium ion | 990 | 415 | Fair | 99.91 | 99.91 | Good |
| Example 7 | 2-Fluoropentane | Ion-exchange resin (1) | Sulfo group | Sodium ion | 1,050 | 35 | Good | 99.95 | 99.95 | Good |
| Example 8 | | Ion-exchange resin (4) | Sulfo group | Sodium ion | 1,050 | 380 | Fair | 99.95 | 99.95 | Good |
| Example 9 | 1,1,1,3,3-Pentafluorobutane | Ion-exchange resin (1) | Sulfo group | Sodium ion | 1,080 | 50 | Good | 99.90 | 99.90 | Good |
| Example 10 | | Ion-exchange resin (4) | Sulfo group | Sodium ion | 1,080 | 430 | Fair | 99.90 | 99.90 | Good |
| Comparative Example 1 | 2-Fluorobutane | Ion-exchange resin (5) | Sulfo group | Hydrogen ion | 1,007 | 600 | Bad | 99.93 | 95.73 | Bad |
| Comparative Example 2 | | Ion-exchange resin (6) | Carboxy group | Calcium ion | 1,007 | 480 | Fair | 99.93 | 99.40 | Bad |
| Comparative Example 3 | | Molecular sieve (1) | — | — | 1,007 | 10 | Good | 99.93 | 99.17 | Bad |
| Comparative Example 4 | 2,2-Difluorobutane | Molecular sieve (1) | — | — | 990 | 8 | Good | 99.91 | 99.80 | Bad |
| Comparative Example 5 | 2-Fluoropentane | Molecular sieve (1) | — | — | 1,050 | 7 | Good | 99.95 | 99.10 | Bad |
| Comparative Example 6 | 1,1,1,3,3-Pentafluorobutane | Molecular sieve (1) | — | — | 1,080 | 12 | Good | 99.90 | 99.30 | Bad |

The following were confirmed from the results listed in Table 1.

In Examples 1 to 10, decomposition of the fluorohydrocarbon compound during dehydration could be suppressed. As a result, a purified product which had a low water content and in which the fluorohydrocarbon compound had high purity could be obtained.

In Comparative Example 1 in which an H⁺-type strongly acidic ion-exchange resin was used, the water content could not be sufficiently reduced. Moreover, the purified product showed a decrease in purity.

In Comparative Example 2 in which a weakly acidic ion-exchange resin was used, and Comparative Examples 3, 4, 5, and 6 in which a molecular sieve was used, the purified product showed a significant decrease in purity.

The invention claimed is:

1. A method for purifying a fluorohydrocarbon compound comprising bringing a crude saturated fluorohydrocarbon compound having 4 or 5 carbon atoms into contact with a salt-type strongly acidic ion-exchange resin to remove water from the crude saturated fluorohydrocarbon compound,
   wherein the salt-type strongly acidic ion-exchange resin is a resin that comprises a cation selected from a group consisting of a sodium ion, a potassium ion, a magnesium ion, a calcium ion, a barium ion and an ammonium ion, and a sulfo group.

2. The method according to claim 1, wherein the saturated fluorohydrocarbon compound having 4 or 5 carbon atoms is a compound of the following formula (1) or (2), $$C_4H_aF_b \quad (1)$$

$$C_5H_cF_d \quad (2)$$

wherein a and b represent a positive integer, provided that a+b is equal to or less than 10, and c and d represent a positive integer, provided that c+d is equal to or less than 12.

3. The method according to claim 1, wherein the salt-type strongly acidic ion-exchange resin is a resin that comprises a cation selected from a group consisting of a sodium ion and a calcium ion, and a sulfo group.

4. The method according to claim 2, wherein the salt-type strongly acidic ion-exchange resin is a resin that comprises a cation selected from a group consisting of a sodium ion and a calcium ion, and a sulfo group.

* * * * *